Figure 1:
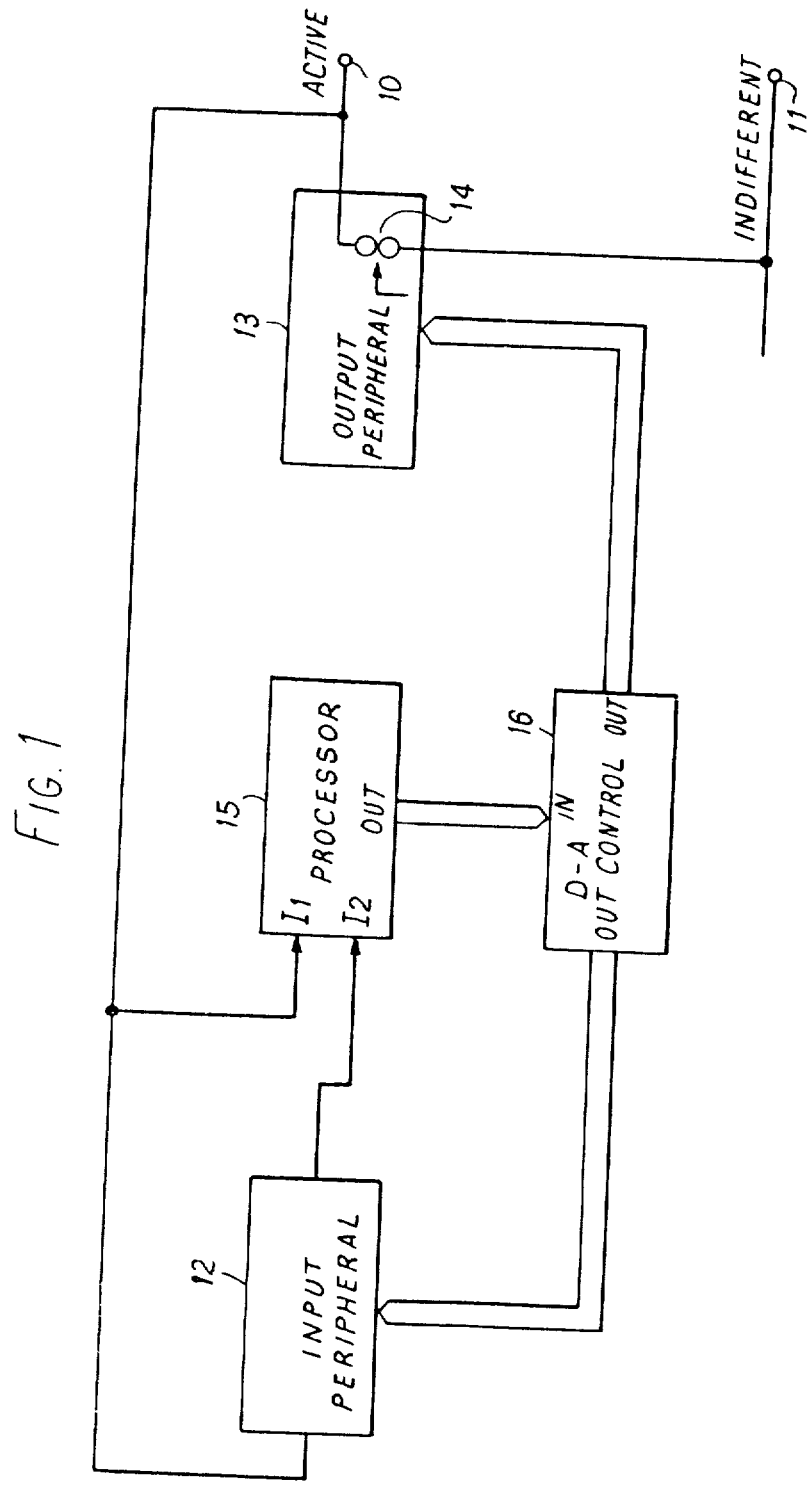

United States Patent [19]

Backhouse

[11] 4,222,385

[45] Sep. 16, 1980

[54] ELECTRONIC HEART IMPLANT

[75] Inventor: Richard J. Backhouse, St. Albans, England

[73] Assignee: National Research Development Corporation, London, England

[21] Appl. No.: 940,327

[22] Filed: Sep. 7, 1978

[51] Int. Cl.$^3$ .............................................. A61N 1/36
[52] U.S. Cl. ............................................. 128/419 PG
[58] Field of Search ................................ 128/419 PG

[56] References Cited

U.S. PATENT DOCUMENTS

| | | | |
|---|---|---|---|
| 3,557,796 | 1/1971 | Keller, Jr. et al. | 128/419 PG |
| 4,126,139 | 11/1978 | Walters et al. | 128/419 PG |

FOREIGN PATENT DOCUMENTS 2738871  3/1978  Fed. Rep. of Germany .... 128/419 PG

*Primary Examiner*—William E. Kamm
*Attorney, Agent, or Firm*—Blanchard, Flynn, Thiel, Boutell & Tanis

[57] ABSTRACT

An electronic heart implant utilizes a digital data processor to perform functions such as determining the heart beat rate and determining instants at which stimulating current pulses are to be injected. Time periods are determined by performance of programs in which machine cycles are counted. Time periods are therefore determined as a number of machine cycles each of known duration. The invention enables a low current consumption heart implant to be provided which, by suitable programming of the data processor, can cater for a wide variety of heart conditions. The specification is also concerned with a novel form of data processor particularly adapted to the required functions in a heart implant.

3 Claims, 17 Drawing Figures

MICRO-INSTRUCTION TABLE FOR EXAMPLE 1

| INSTRUCTION NO. | INST A | INST B | STROBES | INST C |
|---|---|---|---|---|
| 0 | (a) OP=0<br>(b) I2 NOT ENABLE<br>(c) LATCH OP VERIFIED<br>(d) PAGE SEL PAGE 1 | | LATCH ENABLE REGISTERS RESET<br>LE ↘  ↙ RR | TRUE PARALLEL<br><br>T P<br>↓ ↓ |
| CODE | (a)<br>0000 | (c)(b)(d)<br>0101 | 0110 | 0011 |
| 1 | SELECT RAM A<br>(C=0)<br><br>0001 | NOT USED<br><br><br>1111 | NOT USED<br><br><br>0000 | WRITE TO A<br><br>WA ↓<br>0111 |
| 2 | SELECT RAM A, 1<br>C=C+1 | SELECT RAM B, 1<br>HOLD 1 | LOAD REGS<br>RCK ↓ | WRITE TO A |
| CODE | 0001 | 0001 | 1000 | 0111 |
| 3 | A,1 = C | B,2 = N | LOAD REGS | |
| CODE | 0001 | 0010 | 1000 | 0011 |
| 4 | JUMP FORCES PROG COUNT TO INSTRUCTION 2 | | CONDITIONAL JUMP | COMPLEMENT REGS ↓ |
| CODE | 0000 | 0010 | 0001 | 0001 |
| 5 | (a) OP = 15<br>(b), (c) & (d) AS PER INSTRUCTION 0 | | LE , RR | |
| CODE | 1111 | 0101 | 0110 | 0001 |
| 6 | ALL HIGHS TO HALT | | UNCONDITIONAL JUMP | |
| CODE | 1111 | 1111 | 0001 | 0001 |

FIG. 8

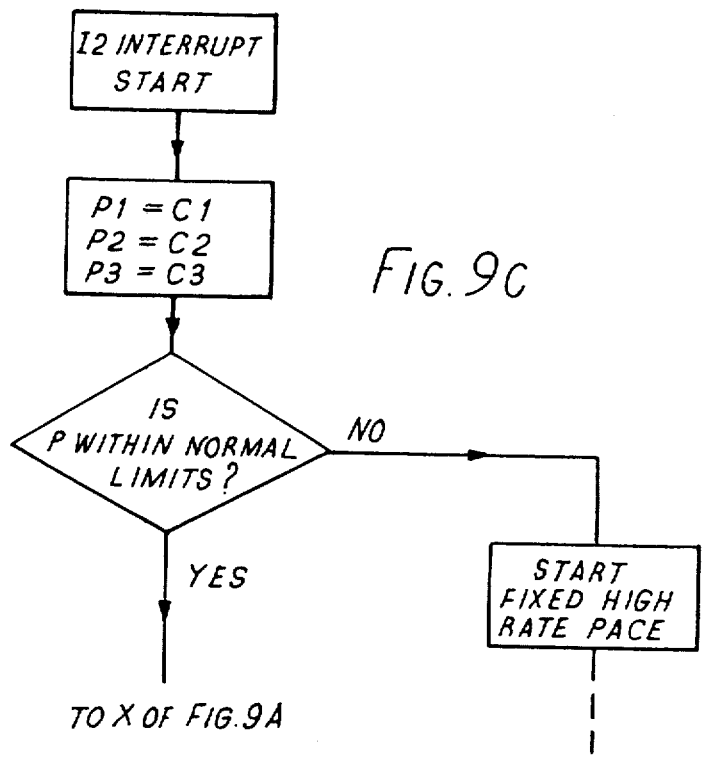
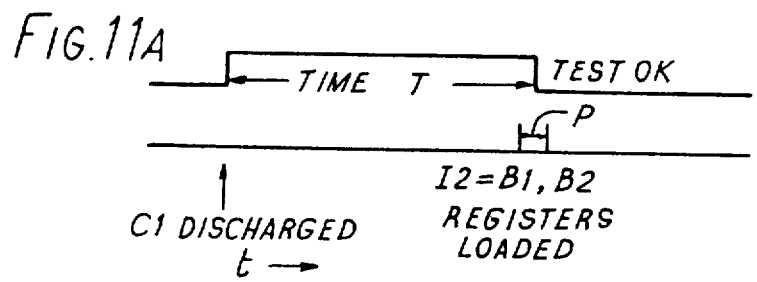
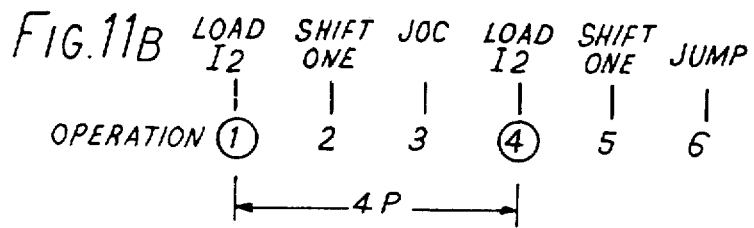

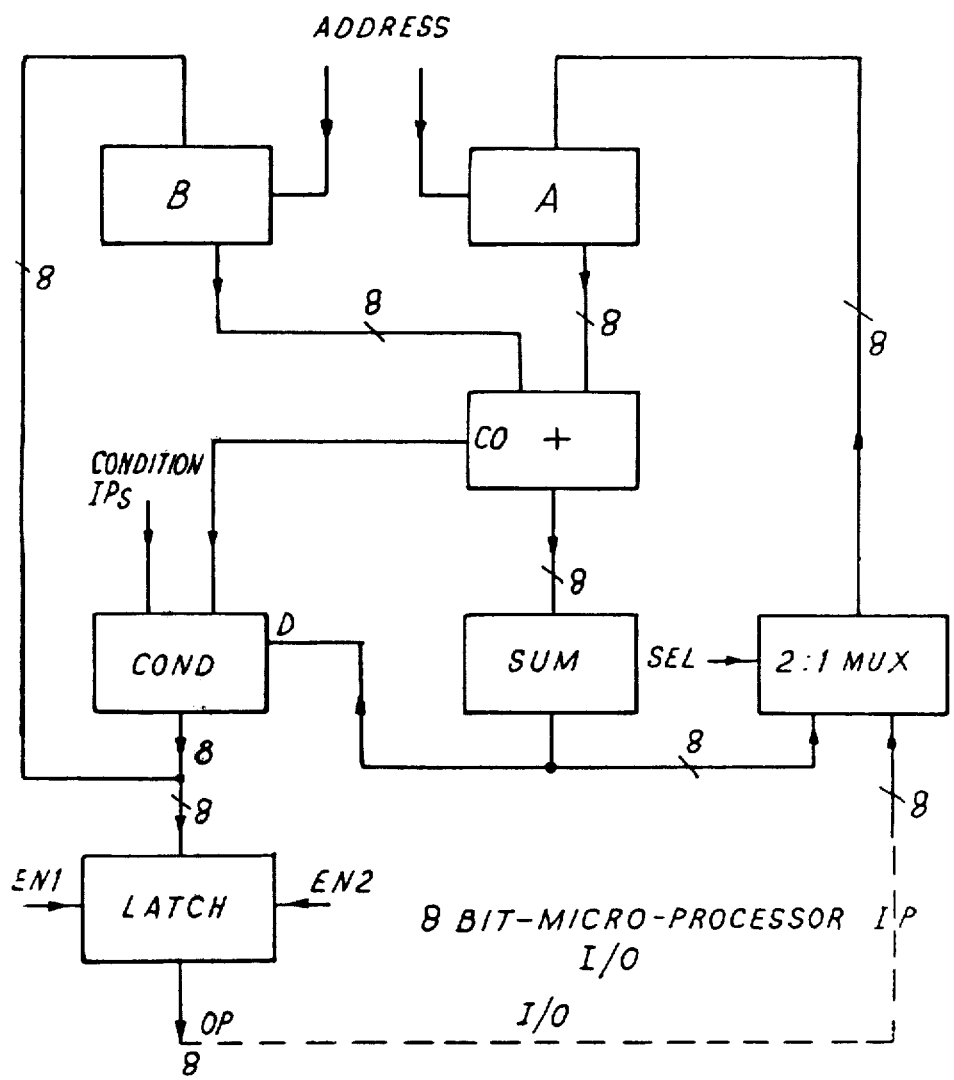

ELECTRONIC HEART IMPLANT

The present invention relates to an electronic heart implant, commonly called a pacemaker, which can be used to control conditions such as bradycardia and tachycardia. It is known to control bradycardia by detecting when the heart rate falls below a certain value and to inject current pulses which stimulate the heart to beat at the required rate. It is also known to control tachycardia by detecting a high rate and injecting a current pulse a suitable time after an R wave; an adaptive process is necessary to ascertain what is the suitable time. It is known to do this by starting with a preset time. If a current pulse injected after this time fails to arrest the tachycardia, the time is varied progressively until a value is found which achieves the required result. This value is stored to become the preset value used when tachycardia is next detected. See Spurrell et al, British Heart Journal, Vol. 35. 1973, pages 113 to 122 and pages 1014 to 1025.

Heart implants can be constructed using analog circuits in which time periods are established by RC time constants. The disadvantages of such circuits is their inflexibility and restricted functional ability for a given current consumption.

It has therefore been proposed to employ digital circuits in which time periods are established by counting clock pulses. Such circuits become complex if they are designed to be able to deal with a variety of heart conditions and the complexity leads to a relatively high current consumption and high cost.

The object of the present invention is to provide an implant which can provide a wide range of facilities without the need for high current consumption and which can be constructed fairly cheaply from commerically available integrated circuits. A further object of the invention is to provide an improved store program digital data processor suitable for use, inter alia, in an electronic heart implant.

Figure 2:
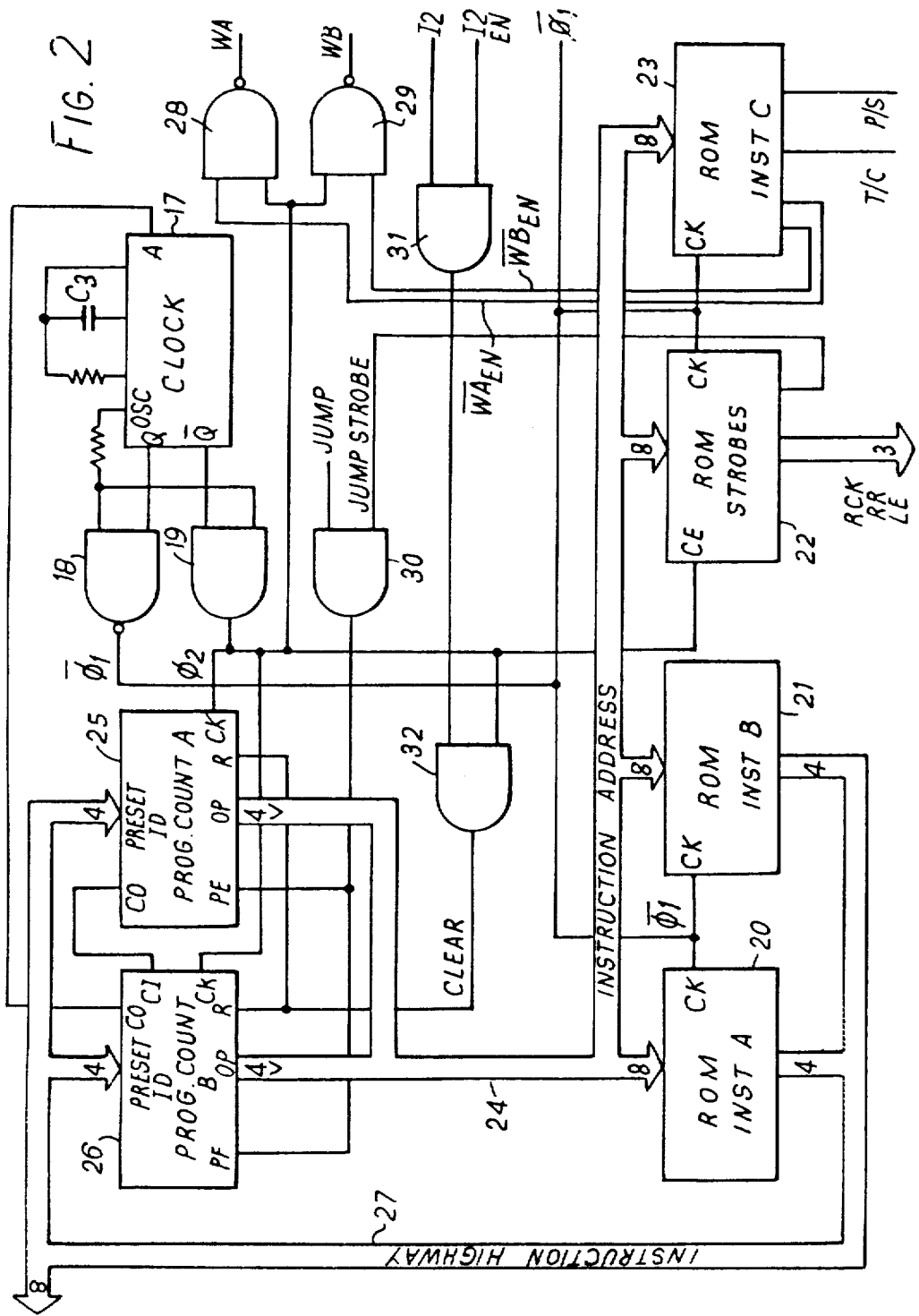
Figure 3:
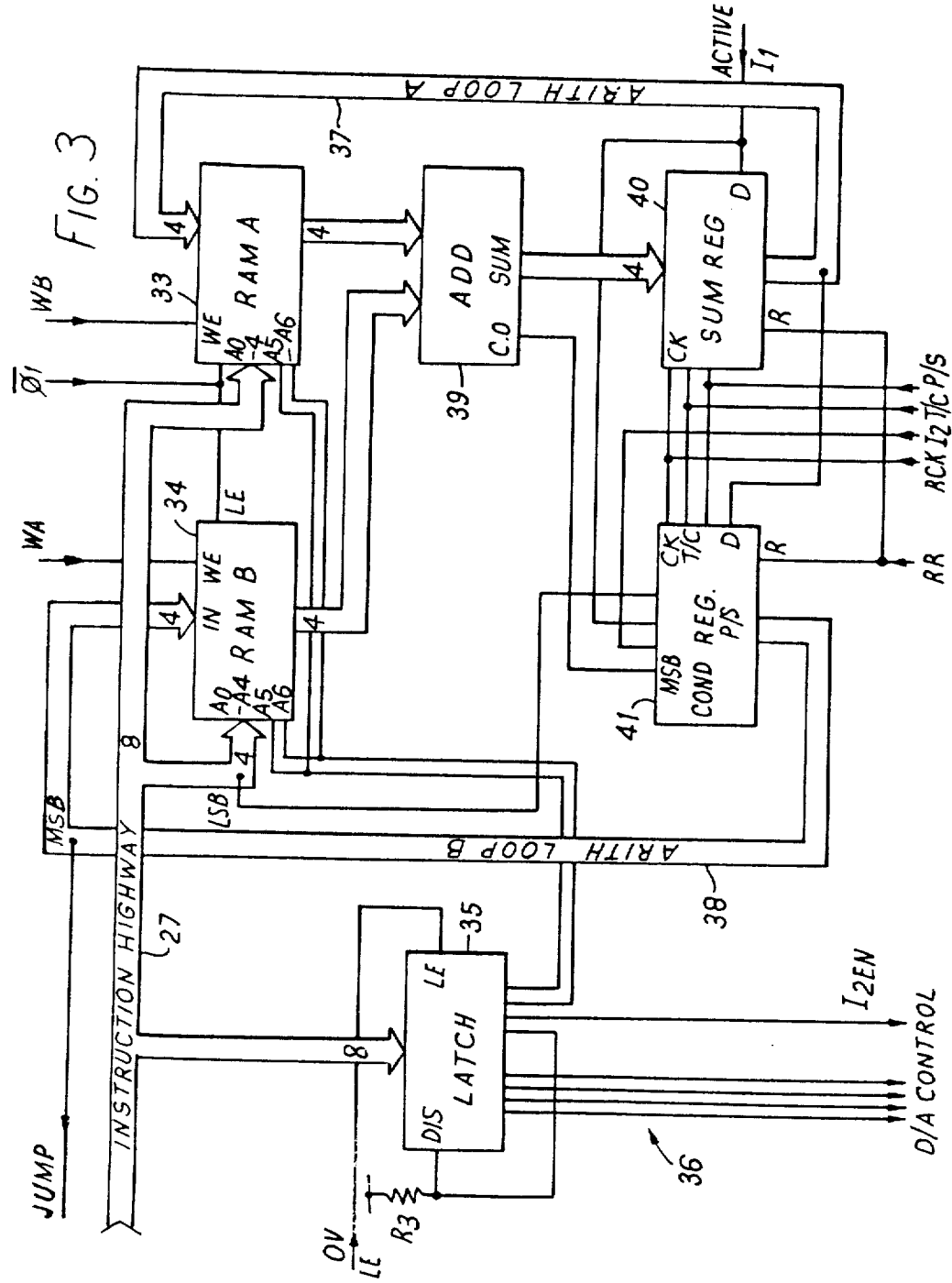
Figure 4:
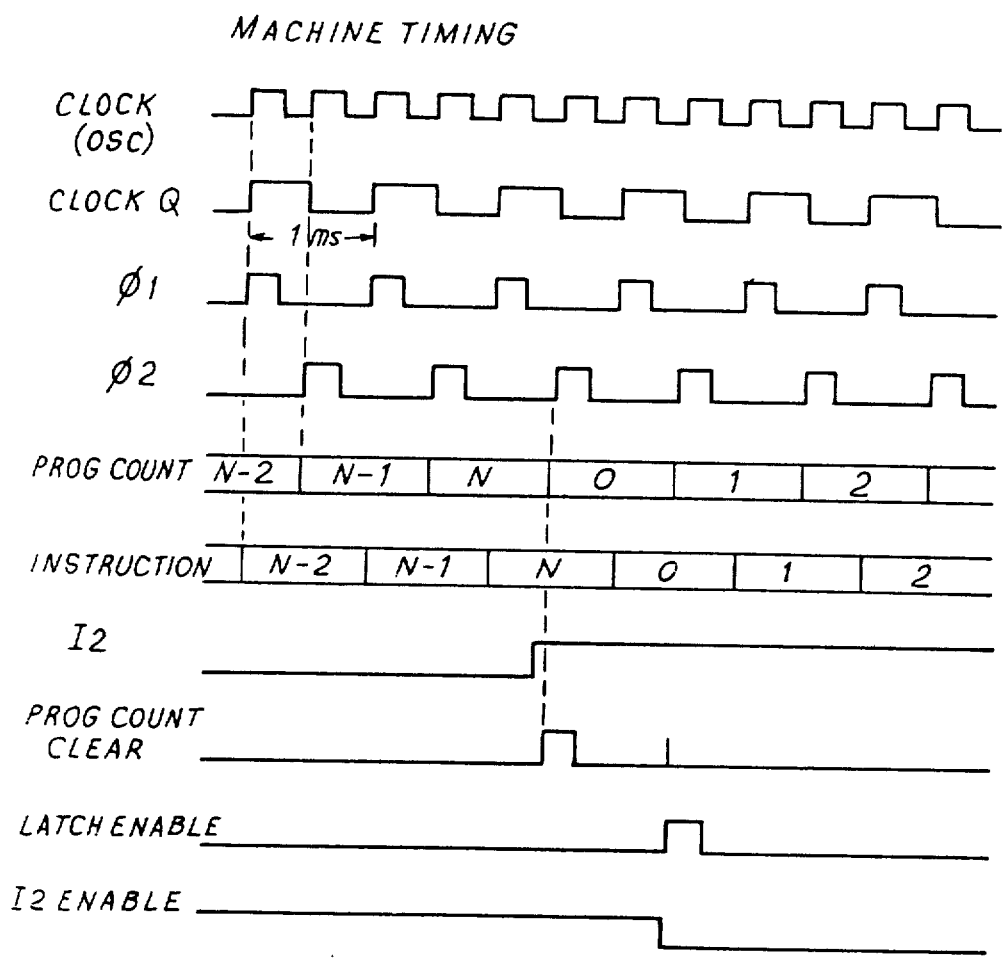
Figure 5:
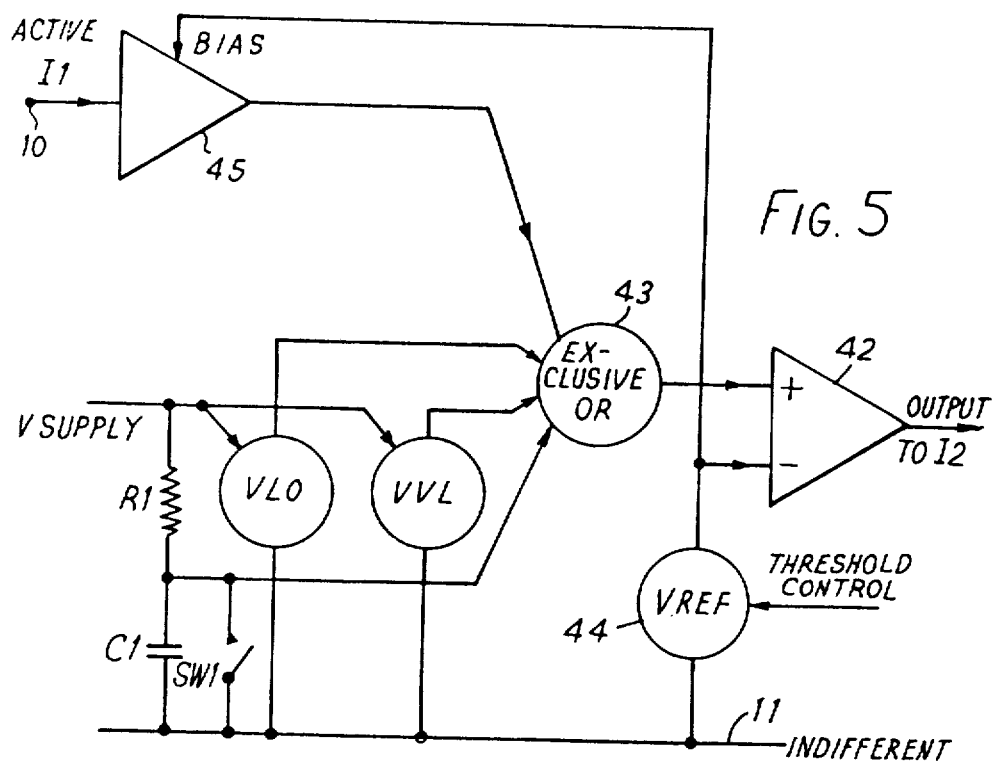
Figure 6:
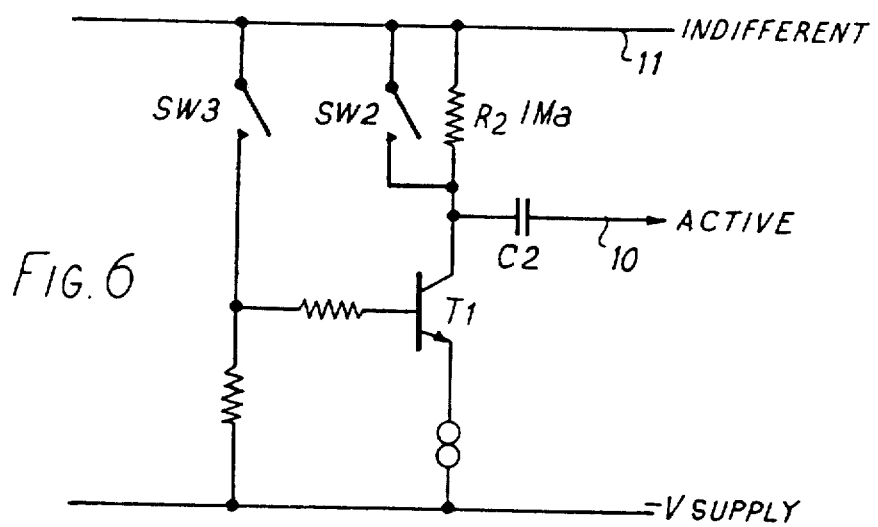
Figure 7:
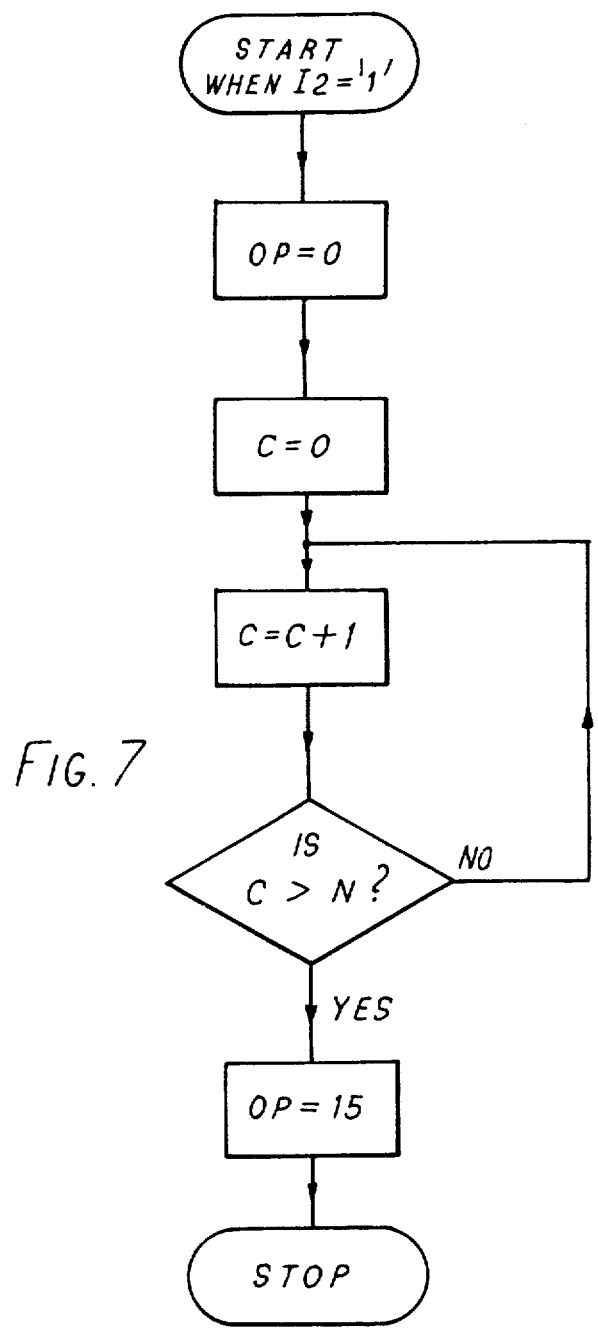
Figure 9A:
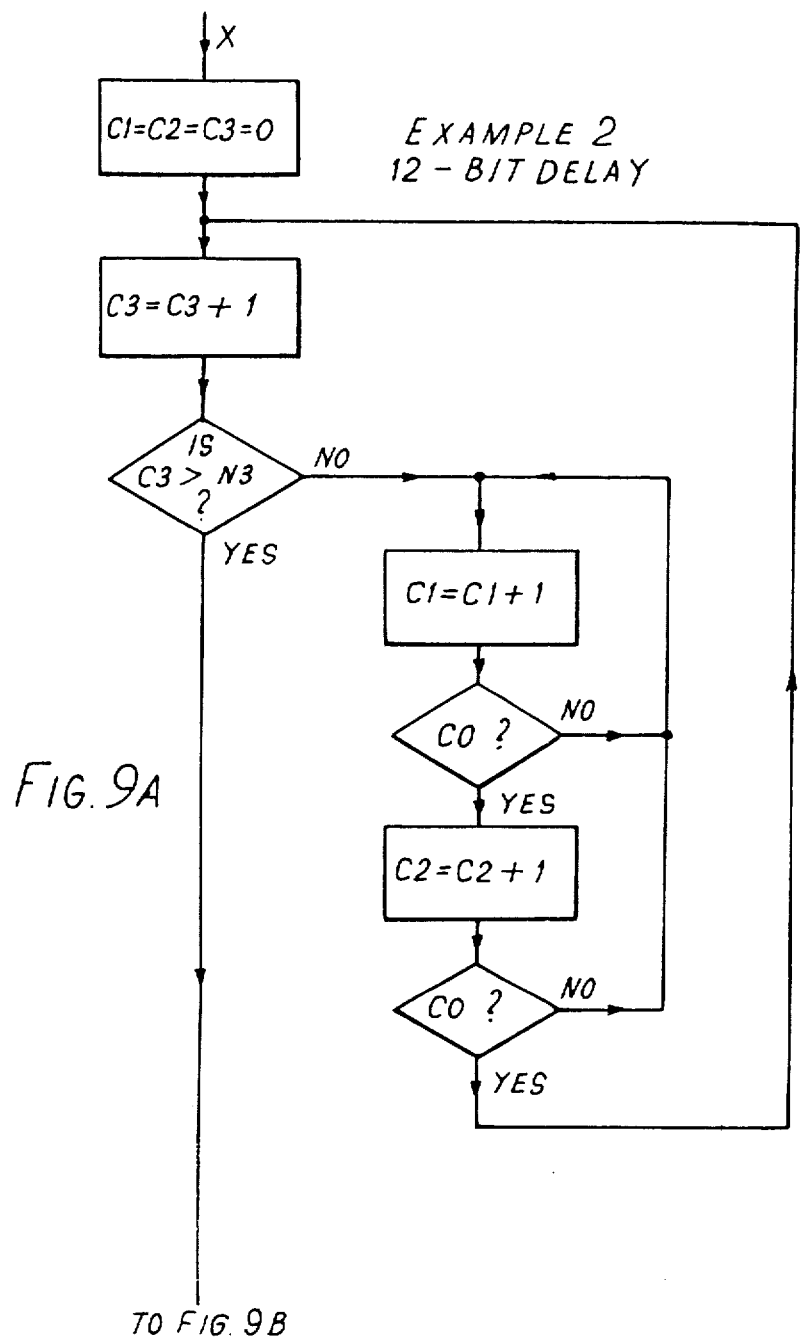
Figure 9B:
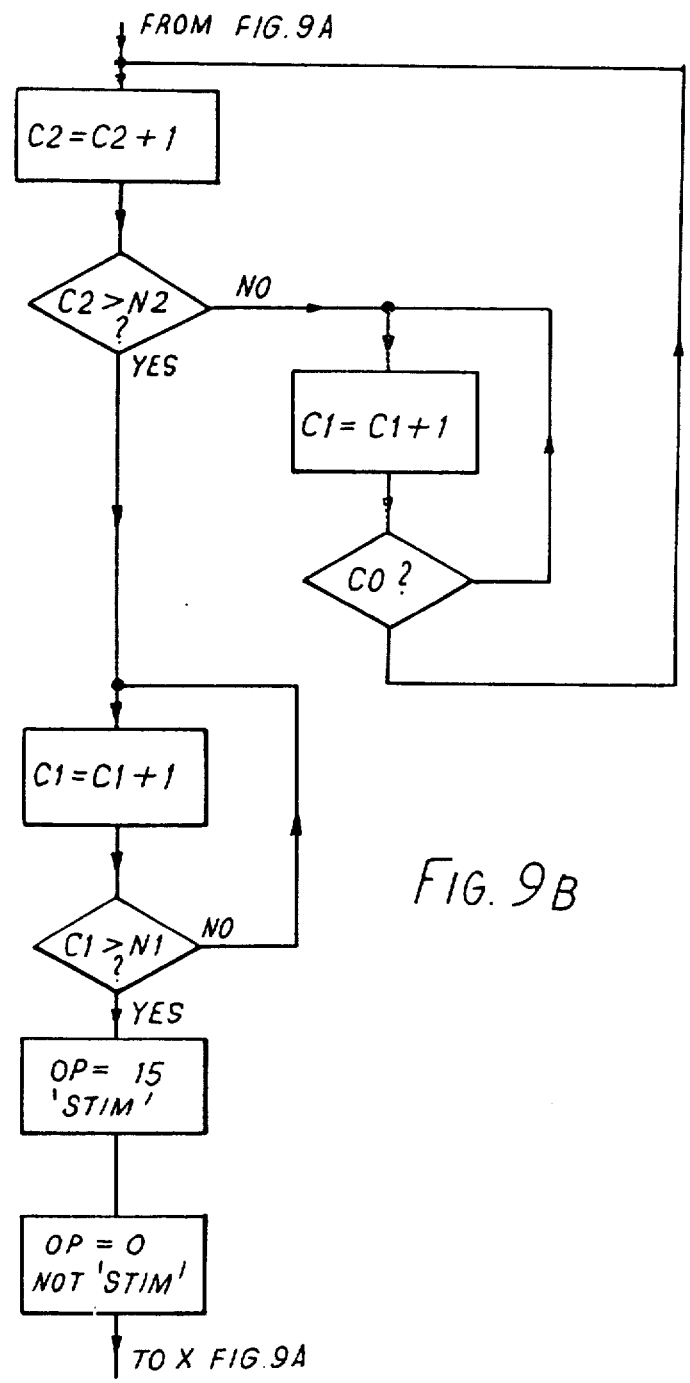
Figure 10:
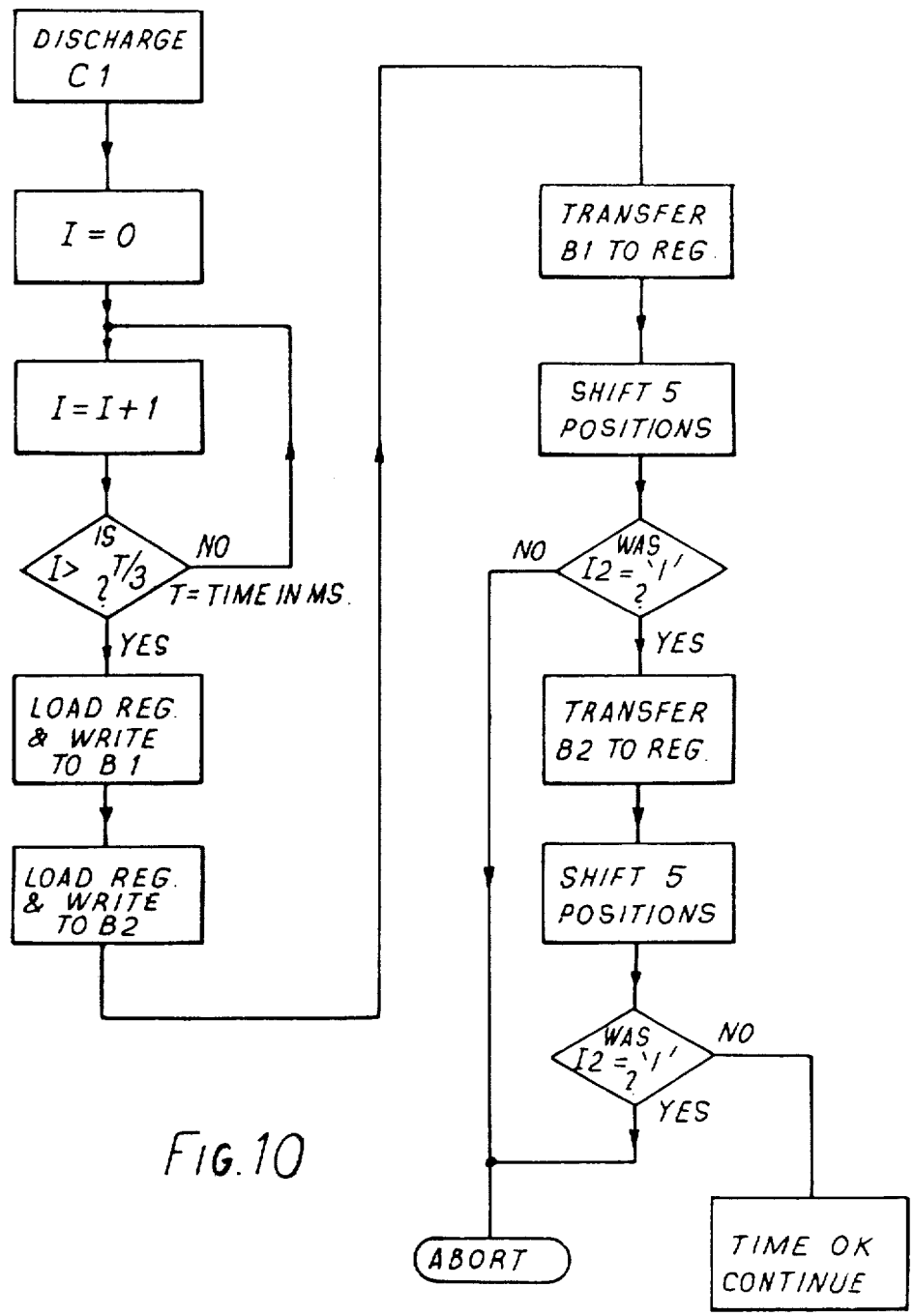
Figure 12:
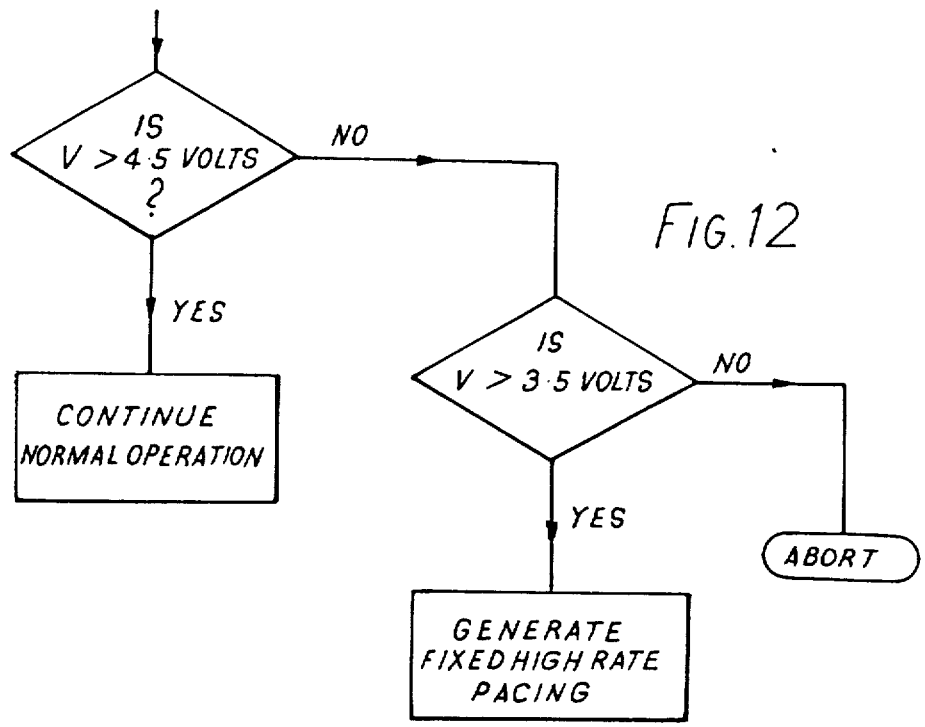
Figure 13:
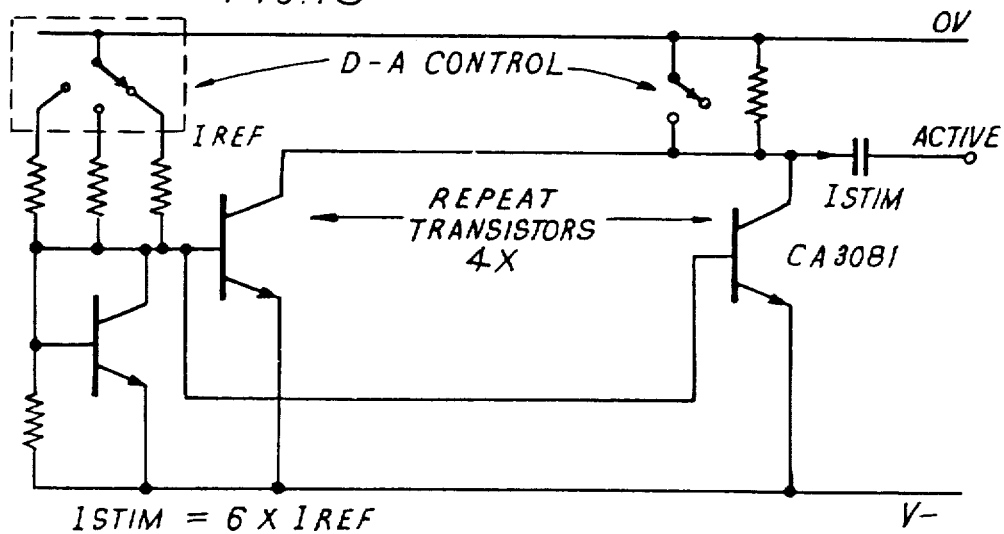

The invention is defined in claim 1 and 5 and will now be described in some detail, by way of example, with reference to the accompanying drawings, in which:

FIG. 1 is a schematic block diagram of an embodiment of the invention,

FIG. 2 illustrates the micro-instruction control circuits of the implant processor, FIG. 3 illustrates the arithmetic circuits of the implant processor, FIG. 4 illustrates timing waveforms of the processor, FIGS. 5 and 6 are diagrams of input and output peripherals respectively, FIG. 7 is a flow chart of Example 1, FIG. 8 tabulates the micro instructions used in Example 1, FIGS. 9A to 9C make up a flow chart of Example 2, FIG. 10 is a flow chart of Example 3, FIGS. 11A and 11B are explanatory diagrams relating to Example 3, FIG. 12 is a flow chart of a battery voltage test, FIG. 13 is a diagram of a modified output peripheral, and FIG. 14 is a block diagram of a modified processor.

Referring to FIG. 1, the implant is connected to the patient in conventional manner by an active electrode 10, which is inserted introvenously in the apex of the right ventricle, and an indifferent electrode 11. The active electrode is an input/output electrode connected to an input peripheral 12 comprising an amplifier and trigger circuit, and to an output peripheral 13 comprising a controlled current source 14 connected between the electrodes 11 and 10.

Operation is controlled by a data processor 15 by way of a digital to analog control 16 which adjusts the threshold of the trigger circuit in the input peripheral and determines the instants at which the current source 14 provides current pulses. The processor has an input I, connected to the active electrode and an input $I_2$ connected to the output of the input peripheral.

The processor 15 comprises a clock 17 (CD 4047). Such references in brackets indicate suitable commerical devices, by way of example, the prefixes CD and MC indicating devices available from RCA and Motorola respectively. The clock establishes the machine cycle of the processor and a suitable clock rate is 2kHz, divided by two to yield a machine cycle of 1ms. The 2kHz square wave (see also FIG. 4) is labelled OSC while the 1kHz square wave is Q. A NAND gate 18 (MC 14011) derives $\phi_1$ from OSC and Q while an AND gate 19 (MC 14081) derives $100_2$ from OSC and $\overline{Q}$ where $\phi_1$ and $\phi_2$ are pulses at 1kHz, out of phase with each other (see FIG. 4).

Instructions are provided by four 256×4 bit ROM's 20 to 23 (each MCM 14524) addressed on an 8-bit highway 24 from two 4-bit presettable binary counters 25 and 26. Terminals of blocks 20 to 23, 25 and 26 are labelled as follows:

CK = CLOCK
CE = CHIP ENABLE
CO = CARRY OUT
CI = CARRY IN
R = RESET (CLEAR)
PRESET = Presetting input to counter (effective in presence of PE)
PE = PRESET ENABLE The counters 25 and 26 are program counters A and B for the lower and higher significance bits respectively. The four ROM's are used as follows:

20 ROM INST A; four bits of an 8-bit instruction on instruction highway 27.
21 ROM INST B; other four instruction bits
22 ROM STROBES; provides four strobe bits defined below.
23 ROM INST C; provides four control bits defined below.

The four strobe bits are:
RCK = REGISTER CLOCK
RR = REGISTER RESET
LE = LATCH ENABLE
JUMP STROBE The four control bits are as follows:
$\overline{WA}_{EN}$, NAND'ed with $\phi_2$ (gate 28) to provide EN
WA = WRITE A
$\overline{WB}_{EN}$, NAND'ed with $\phi_2$ (gate 29) to provide
WB = WRITE B
T/C = INVERT REGISTER OUTPUTS (i.e. "True" or "Complemented")
P/C = PARALLEL/SERIAL These functions will all be explained below.

the AND (gate 30) of a signal JUMP and JUMP STROBE provides PE to preset the counters 25 to 26 to the bits then on the instruction highway 27.

The signal $I_2$ from the input peripheral is used in the presence of $I_{2EN}$ (see below) and of $\phi_2$ (gates 31 and 32) to provide the CLEAR signal to the counters 25 and 26.

Referring now to FIG. 3, the arithmetic section of the processor is centered on two 64×4 bit RAM's 33 and 34 (MCM 14552) each with six address bit terminals $A_0$ to $A_5$. The RAM's are denoted RAM A (33) and RAM B(34). They have write enable terminals WE receiving WA and WB respectively. $A_o$ to $A_4$ of RAM A and RAM B are provided by the eight bits on the instruction highway 27 while $A_4$ and $A_5$ are provided in common by two of the bits of an 8-bit latch 35 (MC 14508). The 8-bit word on the instruction highway 27 is entered in the latch 35 in the presence of latch enable LE.

The other six bits of the latch are used as follows. One bit is the aforementioned signal $I_{2EN}$. Four bits on lines 36 feed the digital to analog control 16 (FIG. 1). The remaining bit is a disable bit DIS employed as explained below.

The inputs to the RAM's A and B are from respective A and B arithmetic loops 37 and 38. The outputs from the RAM's feed a 4-bit full adder 39 (MC 14008) whose sum output is fed to the bit-parallel input of a 4-bit sum register 40 having a parallel output feeding the A arithmetic loop 37. This register and a condition register 41 (both MC 14035) are shift registers, with shift clock terminals CK responsive to RCK, capable of conversion to parallel input and output under control of P/S, and with the facility of inversion of the parallel output bits under control of T/C. The parallel output from the condition register 41 drives the B arithmetic loop 38 and the most significant bit (MSB) thereof provides the signal JUMP.

For serial, shift register, operation each register 40 and 41 has a data (LSB) input terminal D. Terminal D of sum register 40 receives the active analog input on terminal $I_1$ while terminal D of condition register 41 is connected to the MSB output of register 40. RR resets or clears both registers.

The parallel input bits of the condition register 41 are, in order of increasing significance:

Least significant address bit from ROM INST B to RAM B
Active input $I_1$
INPUT peripheral output $I_2$
Carry CO from adder 39.

The input peripheral 12 is shown in FIG. 5. The signal $I_2$ is provided when the input to a comparator amplifier 42 from a selector switch 43 exceeds a reference voltage $V_{REF}$ provided by an adjustable source 44 set by a threshold control signal from the D/A control 16. The main input to the switch 43 is the output from a sensing amplifier 45 (with bias set by $V_{REF}$) whose input ($I_1$) is connected to the active terminal 10. The other inputs to the switch 43 are from a test circuit 46 comprising a resistor $R_1$, capacitor $C_1$ and switch $SW_1$ (in practice a semiconductor switch), a voltage source $V_{LO}$ and a voltage source $V_{LL}$ providing voltages proportional to the supply to set up voltage low and voltage very low tests. The switch 43 is controlled by the D/A control 16 to determine which of the four inputs is applied to the amplifier 42.

The output peripheral (FIG. 6) comprises a constant current source 46 in series with a switching transistor $T_1$ and a 1 megohm reistor $R_2$ across the active and indifferent terminals 10 and 11 but decoupled by a 10uF capacitor $C_2$. $T_1$ is turned on when switch $SW_3$ is closed. $SW_2$ is closed to discharge $C_2$ after injection of a current pulse. $SW_1$, $SW_2$ and $SW_3$ are all controlled by the D/A control 16 which decodes its 4-bit input to provide up to 16 analog control operations, i.e. control of the switches (including switch 43) and of the threshold level $V_{REF}$ (FIG. 5).

Although the architecture of the processor is not conventional, overall organization is based upon conventional computer design practice. Salient features are that:

(a) Words are processed in a parallel form.
(b) Processing is controlled by instruction words held in and read out from a ROM store in a logicaly controlled sequence.
(c) Progress through the instructions is controlled by a binary program counter which is incremented by a clock generator, the rate of which provides the basic machine timing.
(e) There is mathematical data storage (RAM).
(f) This data can be modified mathematically and re-stored (Arithmetic Logic Unit, ALU FIG. 3).
(g) Data can enter or leave the system under the control of the program (I/O operation).
(h) A jump (or branch) to any part of the program can be made on condition of the result of a prior operation or input state. The jump can also be made unconditionally.

Briefly, the processor processes mathematical data in four-bit word lengths. This form has been chosen to minimise the chip count, as most micro-circuits from the Motorola McMOS range are four bits wide. Instructions are stored in the four ROMs. This gives a capacity of 256 instruction words 16 bits long. The ROM address or instruction number is provided by an eight-bit presetable counter which is incremented at the rate of 1 kHz, set by the master clock. The counter is forced to a new instruction number when a preset is issued by way of a Jump command. Mathematical data (or working data) is stored separately from the instructions in the two 64×4 bit RAMs. This data can be modified by the adder (four bits wide) so that the content of RAMA (addend) can be added to the content of RAMB (augend). The result can be stored pro tem in the register 40, 41 before being written back into the RAMs or otherwise used.

Considering operation in more detail, each 16-bit instruction word is divided into two fields. One field contains addresses which select RAM locations or addresses to which the program must jump when a branch procedure is executed or which form the word to be latched. The control field, may be considered as two parts of four bits per part. Strobe pulses presented for purposes of instantaneous control, ie. the timing between discreet operations, are controlled by four bits which are produced by clock phase $\phi 2$ operating the CE (chip enable) control of ROM strobes. If, for example, bit RCK of ROM Strobes is High then there will be a pulse on line RCK coincident with pulse $\phi 2$. FIG. 4 shows the timing relationships. The remaining four bits of the control field set up states in the processor prior to a Strobe pulse so that stable conditions in the circuit exist before and during the Strobe period.

The Micro-Instruction Store address is generated by the eight bit counter Prog Count. This counter is incremented by the $\phi 1$ pulse, so that successive instructions are progressed sequentially. A jump in the instruction sequence is achieved by loading the counter, Prog Count, to a new address word held in the address field of that instruction by operating the preset enable PE of the counter with a jump command pulse.

The Working Data Store (FIG. 3) is formed from RAMA and RAMB. The store address is controlled by the address field section of the instruction word. Four bits of the field operate RAMA and the other four bits RAMB. This gives 16 independent four bit word locations in four pages for either store. The pages are selected by the states of the address lines A4 and A5. The states are controlled by the Latch 35.

So, to summarise, the addressing arrangement for RAMs A and B require the same page to be selected for each RAM. Within the selected page, one word of RAMA may be selected independently of the word of RAMB, e.g.:

|        | RAM A   | RAM B   |
|--------|---------|---------|
| Page 2 | WORD 3  | WORD 10 |
| Page 1 | WORD 10 | WORD 10 |
| Page 4 | WORD 0  | WORD 5  |
| Page 0 | WORD 9  | WORD 15 |
| Page 2 | WORD 3  | WORD 7  |

The outputs of RAMS A and B are added (four bit parallel) in the adder 30. The result of the addition will be stored in the SUMREG 40 when this register is placed in the parallel mode by a High on the P/S line and clocked by a pulse on the RCK line. The output of SUMREG can be written into RAMA by a write enable pulse on line WA. RAMA has outputs which are latched by the signal $\bar{\phi}_1$ during the write enable period, so that a read while write operation is possible. The advantage of this will become apparent as I proceed with the description. The second shift register CONDREG is provided to store conditional data, i.e. data that results from particular operations such as the overflow CO from the adder, which is fed to bit $2^3$ parallel input of CONDREG, or the input states from the lines $I_1$ and $I_2$ or the LSB of ROMB so that contents held in ROMB can be entered to CONDREG. The output of CONDREG may be written to RAMB independently but in the same way as data are written to RAMA. The two registers may be operated in serial mode by placing the P/S control Low. Data may then progress by a one bit shift left per clock RCK. Data may enter (via $I_1$) the registers and be routed to RAMA or RAMB under the control of the micro-program.

Branch Control is achieved by gating the most significant bit (MSB) of the CONDREG output with a strobe pulse dedicated to this purpose. If the CONDREG MSB is High then the counter, PROG COUNT, is set at a time coincidence with the JUMP strobe (FIG. 4) by the pulse of the PE line to the word contained in the address field at the time of the JUMP strobe. The next instruction to be executed will be the new address word. If the CONDREG MSB was Low at the time "JUMP strobe" then, cleary, no branching would occur and the next instruction will be the succeeding one. Any bit of a word held in the registers may be used to control a branch instruction by shifting the appropriate bit to this MSB position.

The Latch is used to staticise words from the address field when the strobe LE is made. The 4 bits from ROMINSTA form, via the latch, the output to the D-A control 16 and those from INSTB govern the internal workings of the processor, as described above.

A 'HALT' is obtained by presetting 255 into PROG COUNT which causes the CO line to go Low which stops the clock, (terminal A, FIG. 2).

A return to a working state may be achieved by clearing the counters with an $I_2$ pulse.

An ABORT condition is provided whereby the operation cannot be restored by the operation of $I_2$ but only by some physical intervention. The ABORT is achieved by loading the LATCH with all Highs (255) possibly at the same time as branching to 255 and stopping the clock (HALT). The resulting High on line DIS disables the LATCH, the outputs assume a high impedance state and the line DIS is held High by resistor $R_3$ (FIG. 3). This feature is considered in more detail below.

The machine operation is best described by some examples of the functions that the device is likely to have to perform as a pacemaker. Our example is the need to produce a step B at a time t after the rise in a step A. Assume that A is presented to $I_2$ and that B is produced via the D-A control 16 by setting all 1s (15) into the output latch. A flow chart of the operation is shown in FIG. 7.

Step 1 $I_2$ goes High, A is true.

Step 2 The following $\phi 2$ clock allows PROG COUNT to clear and the instruction address becomes zero. $I_2$ has interrupted the previous sequence.

Step 3 Instruction word zero is available from the front edge of $\phi 1$. The address field of this word is to be loaded to LATCH. The word that is to be held in the latch specifies three separate requirements:
 (a) An output word of zero (OP=0).
 (b) An inhibit of $I_2$, so that the clear on PROG COUNT is removed.
 (c) Selection of the appropriate page. That is the section in RAMS A and B where the work is to be done.

Step 4 During $\phi 2$ the latch is enabled from strobe LE and the address field of the instruction word zero is written to the latch. At this point OP is set to O, B=0.

The registers COND & SM are set to zero by a strobe RR.

Step 5 PROG COUNT increments on the front edge of $\phi 2$.

Step 6 Instruction 1 is available from the front edge of $\phi 1$ and reads as follows:
 (a) Select the location in RAMA where the variable C is to be written.
 (b) Write the zero, obtained by the RR strobe operation on SUMREG, to RAMA (C=O) re Step 4.

Step 7 The write enable to RAMA occurs at $\phi 2$.

Step 8 Instruction 2 selects the location in RAMB where a constant 1 is held (the 1 has been pre-loaded) and the location in RAMA where C is now held. The sum of A+B, i.e. C+1 is loaded to SUM REG and this sum written back to location C so that C=C+1. Writing occurs during $\phi 2$.

Step 9 Instruction 3 reads:
 (a) Select the location in RAMB where the modulus of the delay, N, is held (N is assumed to have been pre-loaded).
 (b) Select C in RAMA.
 (c) Load registers with N+C (COND & SUM load together from RCK).

Step 10 Instruction 4 inverts the outputs of COND & SUM and issues a command to Jump back to Step 8, instruction 2, should there by a High on the JUMP line. A branch to instruction 3 will occur at this point if a no carry condition resulted from the A+B operation of Step 10, if N+C<16. 'The jump-to location' is specified by the address field, which in this case will be 3.

Step 11 Should a carry result from the N+C operation then the program continues with the next instruction, instruction 5.

Step 12 Instruction 5(a) latches 15 to the output and B=1.
(b) places the registers COND & SUM in an all High condition by an RR strobe and holding T/C Low, the inverted mode.

Step 13 Instruction 6 places all ones (255) on the instruction highway and an 'unconditional jump' operation is performed. The number 255 is loaded to PROG COUNT which places the machine in the halt mode, and no further operations can take place until the counter is reset. However the counter cannot be reset because the input $I_2$ is inhibited as from instruction O, re Step 3 (b), so that a permanent lock out situation is produced, which may be useful in this cardiological application since the function of the device may be aborted if automatic self-diagnostic checks prove a malfunction. These checks will be discussed later. The lock out may be circumvented by enabling the input $I_2$ at instruction 5 thus allowing the procedure to repeat.

FIG. 8 tabulates instructions 1 to 6.

At this stage it may be worth considering a value for the delay modulus. A 'greater than' or 'less than' decision is obtained from the sum of two four bit words by examining the presence of a carry and then branching.

If A' B>15 = CO=Branch
then A>(15−B)=CO=Branch
15−B=complement of B=$\bar{B}$
so that A>$\bar{B}$=Branch In the time generating example the decision, is C>N?, is in fact performed by the operation C+$\bar{N}$>15=true to branch. The modulus is therefore written as 'not true,' i.e. as the commplement of N. Let us on an arbitrary basis set up a delay of 24 ms. What will be the value for N and hence $\bar{N}$ the constant held in RAMB? Referring to the flow chart of FIG. 7 and the operation steps, it can be seen that there are two instruction executed between the interrupt 12 and the C=0 operation, taking a total of 2 ms.

Let us now consider the delay around the 'No loop,' i.e the conditional jump to instruction 2 so that C is incremented. Implementing C=C+1 is a single operation worth in time 1mS. The decision C>N? requires two clock periods, one to sum C+$\bar{N}$ and the other to branch or continue. The total loop delay is therefore 3 mS. One more operation is needed to set OP=15. If N were unity ($\bar{N}$=14) then OP=15 when C=2 and the delay will be 2+3×2+1=9mS.

Delay $t = 3(N+1)+3$ ms $= 3(N+2)$ms $\therefore N = (t/3) - 2$

In our example t=24mS $N = (24/3) - 2$ $\bar{N} = 15 - 6 = 9$

A resolution of 3 mS is possible with this algorithm. A 1 mS resolution may be obtained by, as it were, padding out the delay with dummy 'no-operation' instructions. If the delay were to have been 26 mS, then two NO-OP instructions could be inserted between the C=0 and C=C+1 operations, see FIG. 7. NO-OP is produced by not strobing. The algorithm of FIG. 7 will give a delay range of 6 mS where N=0 to 51 mS when N=15. The modulus may be enlarged to yield longer delays by storing N in four bit sections in different locations of RAMA. Example 2 of FIG. 8 illustrates this procedure.

The micro-instructions used in example 1 are tabulated in FIG. 8. The microcode, written in binary form, represents the actual pattern stored in the ROMs.

It is a requirement of an 'R wave inhibited' pacemaker to be able to monitor the R wave period. This can be achieved by the processor by using the count, C, which was set up for producing a delay, Example 2. If the R wave is used to interrupt a current sequence via 12 and instructions P1=C1, P2=C2, P3=C3 are inserted before instruction C1=C2=C3=1 (see FIG. 9C) then P1, P2 and P3 will contain a word representing the period T between the last two R waves, where T=3(16²P3+16P2+P1+4)mS. The range of T will be 12 mS when P1=P2=P3=0 to 12.297 seconds when P1=P2=P3=15. The range is resolvable in increments of 3 mS. These parameters are considered adequate for the anticipated applications. Having obtained this value of C from which the interwave period may be deduced, what use can be made of it? If in the algorithm of Example 2 FIG. 9C we insert instructions which test the size of C before the C=0 instruction (see FIG. 9A) we can determine whether C is inordinately short and caused, perhaps, by an interfering artefact and then take appropriate action by directing the machine to another routine which could ask to look at a succession of intervals and if all are short then generate a group of fixed pacing pulses, thus emulating the behavior of the 'demand' pacemaker under interference conditions (Fixed High Rate Pacing). Setting the output to 15 may be interpreted by the D-A control 16 as a command to turn on the current generator to supply a stimulus to the heart. The next instruction culd set OP=0 (i.e. the last instruction of FIG. 9B), turning off the current. Therefore a current controlled pulse of 1 mS duration will have been generated at time t after the R wave, provided the interwave period is greater than t. The functions just described are all that would be required to perform 'demand pacing' action while disregarding a battery run-down procedure.

In this Example t=(515N₃+35N₂ +3N₁+12)mS where $N_1$, $N_2$ and $N_3$ are stored in three locations and tests such as, IS C3>N3? are overflow tests.

The general safety criteria for a pacemaker are as follows:
1. It is imperative that under no circumstance should the heart be subjected to a direct current greater than 50 μA or a continuous pulse repetition rate greater than 100 P.P.S.
2. That the patient should be made aware of impending battery exhaustion and that a patient with 'heart block' is paced artificially when a loss of 'sensing' results from EM wave interference.

A fail-safe guidline used in pacemaker design is that none of the conditions outlined in 1 should be caused by the malfunction of a single component. A hazardous condition can only arise if a certain combination of components fails. This procedure, coupled with a rigorous investigation as to the reliability of components used, has been proved by experience to be an adequate safeguard.

The processor has been designed to meet the above criteria. In the circuits for the input/output peripherals FIGS. 5 and 6, the 10 μF decoupling capacitor $C_2$ between the electrode and the machine is selected for a leakage current at 5V of less than 0.1 μA. The positive end of the capacitor is returned to indifferent via resister $R_2$. In the absence of an output pulse a DC current of greater than 50 μA could only arise if C had a low shunt resistance and transistor T1 was on continuously, needing two simultaneous failures of a particular combination.

A procedure for protecting against a high rate of stimulation is more involved. The problem may be resolved into two areas of possible failure:

(a) The clock runs too fast (e.g. timing capacitor $C_3$ in FIG. 2 goes open circuit).
(b) The processing logic fails.

The condition (a), i.e. the clock going too fast, could be guarded by an independent time check performed on the clock period. Referring to FIG. 5, a separate time function is generated by discharging C1 from the D - A control 16 by operating $SW_1$ momentarily. As $C_1$ is recharging the comparator is positive and $I_2$ is High for a time determined by the product $C_1$, $R_1$. This time is compared with a set number of clock cycles (the number of cycles determines the accuracy of the test), by ensuring that $I_2$ is High at N and is Low at N+1 where N=number of clock cycles tested. The state of $I_2$ is tested by loading it in the COND register and transferring this data to RAMB (one operation), then loading the register again and transferring to RAMB but into a different location so that the states of $I_2$ are stored in RAMB for a one clock period. This could then be examined at any time by placing the appropriate contents of B back into the registers and shifting left until the bits containing the $I_2$ state information are most significant and could be used to make the jump decision.

Note: The contents of A or B may enter SUMREG unmodified by adding zero, i.e. if B is to enter SUM then A must equal zero. FIG. 10 shows the flow chart for this procedure, and FIG. 11A represents the timing sequence. An incorrect comparison invokes the 'passive stop' instructions HALT and ABORT by jumping to 225; the resulting carry from the program counter stops the clock. The operation could be carried out simply by examining the state of $I_2$ in real-time by:

1. Loading the register
2. Shifting one. 3. Jumping and if positive repeating the procedure.

This procedure would generate a test interval of 4P where P is the clock period, (see FIG. 11B), so that the test time has to be four times as long for a given accuracy.

(b) A condition where the processor logic fails.

The time test and other tests could be performed in a sequence occuring before the functional operations, thus the logic of the machine would have been tested before a stimulus is generated. If these initial tests proved negative (not OK) the machine stops and all functions thereafter are aborted. In the flow chart of FIG. 10 (Example 3) the decision to stop has been deliberately designed to test both 'Yes' and 'No' results so that if, say, the logic is stuck at 'Yes,' the machine will pass the first test but fail the second, and if stuck on 'No,' will fail the first. This introspective procedure provides a good first line defence against dangerous failure but cannot be totally relied on to find all possible faults.

The Latch stands sentinel between the processor and the outside world. It allows a stimulus command at a prescribed time and of a set duration. Should the latch fail, will it fail safely? If the latch stuck at a stimulus command word, the direct current to the 'active' will be blocked by C and the situation is safe. However, if the LATCH enable control LE failed in the enabled state or was operated incorrectly due, perhaps, to a fault in ROM STROBE then a dangerously high rate of stimulation might be produced inadvertently. As a protection against this contingency the LATCH has been made self disabling (ABORTMode). Referringto FIG. 3, the LATCH output DIS may be used to disable the LATCH such that if D is ever High all the LATCH outputs are high impedance, (Tri-state), and in that condition it will remain since R will now hold this disabled state. Outputs other than DIS will be left to float, now outside the influence of the internal workings of the processor. LATCH operation may only be restored by intervening to hold line DIS Low. This disabling function is circumvented by always loading a Low to the LATCH on bit DIS, then, should an incorrect load take place, there is a good chance that a High is loaded to DIS and the circuit function aborted.

If in the course of operation a malfunction is detected, e.g. a clock period error, then both the HALT and ABORT may be invoked as a double precaution. Unused ROM locations could contain the HALT and ABORT instructions so that if some of the instructions become garbled there is an improved chance of the machine finding it way quickly to the ABORT condition. It is proposed that inherent failure safety would be best verified by 'Monte Carlo' simulations, whereby the processor can be subjected to random word instructions, and the resulting stimuli commands examined for hazardous conditions.

In order to satisfy the requirement 2—that of signifying that the battery life is about to end—a means of testing the battery voltage (5 volts normal) will be required. This may be performed by the comparator by switching a proportion of the supply voltage reference (see comparator description below and FIG. 5). If the test shows the battery to be low then the program could jump to a 'Fixed High Rate' routine, i.e. a pacing rate higher than normal, about 90. P.P.M, so that the patient would become aware of this abnormality. As the device may fail unpredictably should the battery voltage fall below the operating requirements of the CMOS transistors, a test should be included for very low voltage (3.5 V) (The CMOS circuits used are specified to 3 V min). If the supply falls to less than 3.5 V then the ABORT instruction could be invoked. The battery test is shown in the flow diagram of FIG. 12.

Words held in the working store RAMs A and B will be of three basic types:

(a) Those that are fixed throughout the life of the device (unalterable constants).
(b) Those that are written in prior to implantation to meet individual requirements (programmable constants).
(c) Those that are altered as part of the processing operation (variables).

Words (a) might written to store during manufacture under the control of a special loading program and, provided that from then on power is always kept on the store and that it is not exposed to undue interference, then the data thus loaded should remain intact. This is why I have suggested that the circuit might be partitioned as per FIGS. 2 and 3. Both parts may be tested and the RAMs loaded autonomously. Words (b) could be loaded as a separate operation at the hospital, if required, to suit, perhaps, an individual requirement.

Let us consider, as an example, the case of the anti tachy/bradycardia proposal where this loading is intended to take place before implantation but after manufacture. The 'active'$I_1$ may be used to input the data. A machine could be used to perform this loading operation, which we call the 'programmer.' The 'programmer' will be connected to the 'active' and preset to the desired parameters. When a load command control is operated the 'programmer' looks for a pulse on the 'active' (stimulus). If a stimulus is present within one second of the load command then the data could be loaded in the quiet period, which occurs after the stimulus when $I_1$ is enabled ($I_1$ being disabled during stimulation). If after one second no stimulus has been generated then the processor is assumed quiet all the time and the data is then loaded. As $I_2$ is an amplified version of $I_1$ both inputs must occur together. The processor has to decide which type of input occurred, and $I_2$ or an $I_1$ and $I_2$. $I_2$ restarts a program run and in that re-run, $I_1$ is tested and if found to be true, i.e. the 'active' is held Low by the 'programmer,' then the processor will go to a load routine which could first initialise the system by issuing a stimulus which would start the data flow from the 'programmer' and the two machines would be in synchronism, and provided the timing of the two devices were matched, then synchronism could be maintained throughout the load operation. Should excessively long loading be encountered then synchronisation could be re-established by the periodic issuing of stimuli from the processor.

To recaptitulate on this 'handshake' routine, the 'programmer' is connected to the processor prior to implantation. The load control is operated. The 'programmer' waits for a stimulus or for one second, whichever is the shorter. The 'programmer' then places $I_1$ in the Low state. The processor acknowledges this input by issuing a stimulus which starts the data flow into $I_1$.

Words (c) have been explained above.

In most computer applications it is more efficient to use subroutines, for a case where a certain routine is repeated a number of times; program storage space is saved by using the one routine in all cases and this is then referred to as a sub-routine, SR. The sequence is usually considered thus. A main program calls a subroutine. When that SR has been executed control is returned to the main program one instruction after the SR call so that the sequence is maintained. It is usual in most computers to store the number to which control must return in a register dedicated to this purpose and this may be considered as being a hardware solution as opposed to the software solution where a 'return' label is stored in RAM prior to a sub-routine call and the label is used to route the control back to the correct point in the main program. I anticipate that sub-routines will be required and, if so, hardware is minimised by resorting to the software solution of 'a return-to' label.

Referring again to the schematic diagram of the input peripheral shown in FIG. 5, the comparator 42 compares an input with a constant voltage reference (V ref). The input may be connected to:

(a) the amplifier 45,
(b) a CR time constant, for performing a time check on the clock, (see above)
(c) one of two potential dividers across the battery which represent the proportion of the supply voltage required for a battery low, VLO, and a battery very low, VVL, test. The switching of these inputs may be performed by a CMOS digital to analog switch DC4066, where two inputs control one of four switches and this would be part of the D-A control 16. The input states are provided by the latch output (see FIG. 1). The comparator output is CMOS compatible, that is $$V\ in\ >V\ ref\ is\ true = 1$$

The amplifier 45 is of a type suitable for amplifying the R wave to a level where it may exceed the threshold offset of the comparator. This offset could be varied through an appropriate operation of the D-A switch 16, hence effecting a change in sensitivity. The low frequency roll off characteristics of the amplifier could be arranged such that R waves of either polarity may be detected, through a double differentiating function so that an amplitude proportional to the rate of the rate of change of the wave is sensed. A sensitivity alteration could be made to compensate for an R wave polarity reversal as part of an algorithm.

The micro-powered operational amplifier number CA3078 is a suitable device for both amplifier 45 and comparator 42.

If the output peripheral is required to control current level, =a genertor as shown in FIG. 13 may be used. The generator may follow conventional lines using bipolar transistors to obtain the current drive of 5–10 mA. In the circuit of FIG. 13, the current can be altered by simply switching in a different references resistor by way of the D-A switch 16. The current mirror principle is used, a transistor array, the CA3081, 7 transistor array is suggested. All transistors are on one chip, so that the collector current V base emitter junction voltages of all the transistors are matched. The current in T1 is set by R1 so that the 'zero impedance' load currents in each of the drive transistors is the same as the collector current of T1 minus the sum of all the base currents. The base currents are supplied by R1.

The design of the processor is based on the utilisation of proprietary CMOS chips from the Motorola McMOS and RCA CD 4000 ranges; bipolar transistor arrays and amplifiers could be taken from the RCA CA 3000 range. Hybrid thick films could then be made with the microcircuit chips and capacitor chips bonded to a ceramic substrate bearing the interconnect pattern with inked resistors printed on to this pattern. Packaging some 22 chips in this way (14 micro-circuits, one capacitor in the processor, three micro-circuits and about 5 capacitors in the I/O peripherals) should present no dimensional problem. However, it is worth considering the power consumption. In the processor there are six chips classified as LSI (Large scale integration); these are the ROMs MC14524 and RAMs MC14552. The manufacturer's data on these devices show a typical mean working consumption at a 1 kHz operation of 7 $\mu$W. Measurements made on one sample MC14524 show a dissipation of 4 $\mu$W at 5 v supply and 1 kHz clock, which is encouraging. Six such chips running at the quoted typical will consume 42$\mu$W. The remainder of the circuit is estimated to comsume about 100 $\mu$W in a working state where the heart is being paced for a bradycardia at 80 PPM.

Power consumption could break down as follows:

---

50 $\mu$W used as stimulation power

-continued

| | |
|---|---|
| 25 μW | in I/O peripherals |
| 25 μW | in processor minus the stores |
| 50 μW | in the stores |
| 150 μW | Total at 5 volts |

At this level of consumption, using mercury cells, a life of four to five years could be expected. The use of a lithium battery should give a life expectancy of ten years plus.

The possibility of integrating the processor into a single chip could yield advantages in size and cost, that is if the anticipated sales were considered to justify the extra investment in developing the special micro-circuits. The degree of integration would also depend on the marketing factor. As a practical minimum I would suggest that all the random logic, i.e. all but the ROMs and RAMs, could be effectively built on a single chip, as the resulting circuit would not be unduly large or complex. This, as a micro-circuit, could have a multiple of general applications other than as a pacemaker if certain changes to the design were made. The next section explains these more general applications and the way in which the processor could be modified to accommodate them.

The described processor differs from a digital computer in one principle respect. The output word is obtained from ROM as part of the instruction set. A computer is an automatic calculator, so that the output must be a direct part of the arithmetic process, i.e. words placed in store and/or stored constants are added, subtracted, multiplied, divided etc. and the results of these operations made available to the output. The present processor on the other hand, is essentially a pulse generator imbued with a certain intelligence derived by performing calculations, the answers of which govern the stimuli but are not required as such by the world outside. To, as it were, universalise the processor it will be necessary to rearrange the circuit so that an output latch is placed on the conditional loop, so that results from calculations can be made available to the output by strobing the latch. To do this no additional circuitry is required. It is a matter of moving the output latch from the instruction highway to the conditional loop. Serial input operations may create bottleneck situations so that a method of parallel 'inputting' to the RAMs would be an advantage. However, this would involve an addition, albeit a small one, of gaining direct access to the Arithmetic loop in order to gain access to store A (contents of A may be transferred to B). The 2:1 multiplexer is suggested as the additional component (see FIG. 14).

A four bit processing format was chosen in order to minimise the chip count. Most McMOS type devices are four bit parallel. However, four bits is inordinately small, a single word giving an incremental of 100/16% = 6.25%, which is too coarse for most applications, causing excessive errors in calculations or restricted ranges in control times unless the words used are made up from multiples of four bits (multiple precision) which requires extra processing at the cost of speed and instruction storage space (see Example 2). An eight bit word would yield an 0.31% incremental. Multiple precision tecniques could always be used should a greater accuracy be required. Therefore, if the circuit were fabricated from special custom built chips then I would suggest an eight bit processor on the lines of the circuit shown in FIG. 14. The control field could be reduced from 8 to 4 bits by encoding the instructions into a group of 16 different operation codes, thus saving 1K bit of memory or one ROM but at the expense of adding a considerable amount of decoding logic.

If in the case of a hybrid thick film fabrication ROM STROBES was removed and an instruction to microcode decoder added the chip count would be increased by 5 or 6. However the decoder would prove the most economic solution in the customised fabrication. Such a micro-circuit could be marketed as a single chip microprocessor consuming negligible power, 25 μW. The possible applications for such a device are innumerable, including implantable aids for the blind and deaf, and data logging in remote locations where the instrument can be expended after five years or so. Data could be filtered intelligently, valuable data stored and transmitted briefly at a set time, or at any time as a warning device. The logger could be used as an ECG monitor on ambulatory patients arrhythmias being selected from normal heart activity and stored in a quantised form within the unit.

The described processor can be compared with the proprietary single chip processors now available. Devices other than those produced from a CMOS technology will have too high a consumption for the implant application. A virtue of the present processor is that a complete operation can be performed for every clock cycle, e.g. operation A+B is performed in one clock period by pulses $\phi 1$ and $\phi 2$. Proprietary single chip processors require multiple clocks per operation, e.g. eight clock cycles to complete one machine cycle, so for a given speed of operation they have to be clocked at eight times the frequency of the present processor, with a corresponding increase in power comsumption. The dissipation of a CMOS gate is in direct proportion to the rate of operation and this, coupled with the relatively high quiescent leakage currents associated with the larger (more transistors) on chip circuit of the proprietary devices, could increase the total device dissipation by a factor of three or more over the described processor, ie. about 500 micro-watts for an operating speed of 1 mS per instruction. There is also the questionable reliability of such a complex circuit. Most of the hardware features will be redundant in a relatively simple application such as the ones being considered here so, despite the advantage of (a) a possibly lower package count and (b) development aids, assemblers, debuggers, prototyping assemblies etc., the single chip processors currently available are not as well suited to the task as the described processor which has been designed for this specific environment.

What is claimed is:

1. An electronic heart implant comprising an input/output terminal for connection to an active electrode in the heart of a patient, a stored program digital data processor including a clock pulse generator establishing a predetermined machine cycle period, an input circuit connected to the input/output terminal to provide interrupt signals to the processor at instants determined by the cardiac voltage waveform of the patient, and an output circuit connected to the input/output terminal and comprising a current source controlled by the processor to inject stimulating current pulses at instants determined by the processor, wherein the processor is arranged to detect abnormal heart conditions by determining the period between interrupts by performance of a program effective to count machine cycles between interrupts and to respond to detected abnormal conditions by commanding injection of current pulses at instants occurring at selected times after previously injected pulses and/or after interrupts, and to determine the selected times by performance of a program effective to count machine cycles, and wherein the processor comprises a store having addressable locations in two store portions, an instruction highway for addressing locations independently in the store portion, an adder adapted to add the contents of two addressed locations in the two store portions respectively, a register arranged to receive the sum provided by the adder and interrupt signals and capable of operation as a shift register, connections for writing the contents of two portions of the register in addressed locations in the two store portions respectively, a program counter arranged to count machine cycles and to address a read-only memory providing instructions on the instruction highway and selectively providing shift pulses for the register and a latch enable signal, and a latch arranged to store the instruction on the instruction highway in the presence of the latch enable signal, the latch being connected to the output circuit to control the generation of the current pulses in accordance with the contents of the latch.

2. An electronic heart implant according to claim 1, wherein the latch is also connected to the input circuit to control a threshold level at which an interrupt signal is generated in accordance with the contents of the latch.

3. An electronic heart implant according to claims 1, wherein one bit in the register and bit selectively provided by the read only memory control presetting of the program counter to a jump address determined by the instruction on the instruction highway.

* * * * *

UNITED STATES PATENT AND TRADEMARK OFFICE
CERTIFICATE OF CORRECTION

PATENT NO. : 4 222 385
DATED : September 16, 1980
INVENTOR(S) : Richard J. Backhouse It is certified that error appears in the above—identified patent and that said Letters Patent is hereby corrected as shown below:

Column 16, line 14; after "register and", insert ---a---.

Signed and Sealed this

Sixteenth Day of December 1980

[SEAL]

Attest:

Attesting Officer

SIDNEY A. DIAMOND

Commissioner of Patents and Trademarks